US012806361B2

(12) United States Patent
Peiris et al.

(10) Patent No.: US 12,806,361 B2
(45) Date of Patent: Nov. 24, 2026

(54) MEDICAL TUBES FOR BREATHING CIRCUIT

(71) Applicant: Fisher & Paykel Healthcare Limited, Auckland (NZ)

(72) Inventors: Telge Nishan Chaturanga Peiris, Auckland (NZ); Paul Joseph Moody, Auckland (NZ); Elmo Benson Stoks, Auckland (NZ); Karla Maree Dey, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 18/453,885

(22) Filed: Aug. 22, 2023

(65) Prior Publication Data

US 2024/0058561 A1 Feb. 22, 2024

Related U.S. Application Data

(63) Continuation of application No. 16/970,510, filed as application No. PCT/NZ2019/050016 on Feb. 22, 2019, now Pat. No. 11,766,536.

(Continued)

(51) Int. Cl.

*A61M 16/08* (2006.01)
*A61M 13/00* (2006.01)

(Continued)

(52) U.S. Cl.

CPC ...... *A61M 16/0875* (2013.01); *A61M 13/003* (2013.01); *A61M 16/06* (2013.01);

(Continued)

(58) Field of Classification Search

CPC .......... A61M 16/1095; A61M 16/0875; A61M 16/08; A61M 16/0816; F16L 11/08–083; F16L 11/112; F16L 11/24

See application file for complete search history.

(56) References Cited

U.S. PATENT DOCUMENTS 3,323,553 A 6/1967 Richitelli et al.
3,794,708 A 2/1974 Richards et al.

(Continued)

FOREIGN PATENT DOCUMENTS

CN 2170950 Y 7/1994
CN 101670952 A 3/2010

(Continued)

OTHER PUBLICATIONS

Translation of DE_202005008156_U1 (Year: 2006).*

(Continued)

*Primary Examiner* — Valerie L Woodward
*Assistant Examiner* — Mautin I Ashimiu
(74) *Attorney, Agent, or Firm* — VIA LLP

(57) ABSTRACT

A medical tube transports gases to and/or from a patient. The medical tube includes a bead wrapped around a longitudinal axis of the medical tube. The bead forms a first portion of a lumen wall of the medical tube. The medical tube also includes a film wrapped around the longitudinal axis of the medical tube. A first portion of the film overlies the bead, and a second portion of the film forms a second portion of the lumen wall. The lumen wall, formed by the bead and the second portion of the film forms a substantially smooth bore. The medical tube can be reusable or reprocessable.

13 Claims, 8 Drawing Sheets

Related U.S. Application Data

(60) Provisional application No. 62/634,360, filed on Feb. 23, 2018.

(51) Int. Cl.
*A61M 16/00* (2006.01)
*A61M 16/06* (2006.01)
*A61M 16/10* (2006.01)
*A61M 16/16* (2006.01)

(52) U.S. Cl.
CPC .... *A61M 16/0808* (2013.01); *A61M 16/0833* (2014.02); *A61M 16/1095* (2014.02); *A61M 16/161* (2014.02); *A61M 2016/0027* (2013.01); *A61M 2016/003* (2013.01); *A61M 2205/3368* (2013.01); *A61M 2205/59* (2013.01); *A61M 2205/6081* (2013.01); *A61M 2206/11* (2013.01); *A61M 2207/00* (2013.01)

(56) References Cited

U.S. PATENT DOCUMENTS

| | | | | | |
|---|---|---|---|---|---|
| 4,304,266 | A * | 12/1981 | Kutnyak | F16L 11/112 138/133 |
| 5,848,223 | A | 12/1998 | Carlson | |
| 6,077,376 | A | 6/2000 | Katraro et al. | |
| 6,347,646 | B2 | 2/2002 | Fukui et al. | |
| 6,367,510 | B1 | 4/2002 | Carlson | |
| 7,156,127 | B2 | 1/2007 | Moulton et al. | |
| 7,870,876 | B2 | 1/2011 | Kanao | |
| 2001/0025665 | A1 | 10/2001 | Fukui et al. | |
| 2008/0202621 | A1 | 8/2008 | Kanao | |
| 2009/0025724 | A1 | 1/2009 | Herron, Jr. | |
| 2009/0078259 | A1 | 3/2009 | Kooij et al. | |
| 2010/0224276 | A1 | 9/2010 | Forrester et al. | |
| 2013/0092277 | A1 | 4/2013 | Garrett et al. | |
| 2014/0000626 | A1 | 1/2014 | O'connor et al. | |
| 2014/0053939 | A1* | 2/2014 | Kaye | F16L 11/112 138/109 |
| 2014/0158130 | A1 | 6/2014 | Coleman et al. | |
| 2014/0332108 | A1 | 11/2014 | Forrester et al. | |
| 2015/0027204 | A1 | 1/2015 | Stoks | |
| 2017/0296769 | A1 | 10/2017 | Smith et al. | |
| 2018/0296787 | A1* | 10/2018 | Maurer | A61M 16/0666 |

FOREIGN PATENT DOCUMENTS

| | | | | |
|---|---|---|---|---|
| CN | 104736336 A | 6/2015 | |
| CN | 106999692 A | 8/2017 | |
| DE | 202005008156 U1 * | 10/2006 | A61M 16/1095 |
| EP | 1535722 | 1/2005 | |
| GB | 1285457 | 8/1972 | |
| GB | 1419841 | 12/1975 | |
| GB | 2325040 | 11/1998 | |
| JP | 2001179822 A | 7/2001 | |
| JP | 4332965 | 9/2009 | |
| WO | WO 2012/122601 | 9/2012 | |
| WO | 2015142192 A1 | 9/2015 | |
| WO | WO 2016/048172 | 3/2016 | |
| WO | WO-2016048172 A1 * | 3/2016 | A61M 16/0875 |

OTHER PUBLICATIONS

International Search Report for International Application No. PCT/NZ2019/050016 dated Jun. 11, 2019.
International Preliminary Report on Patentability for International Application No. PCT/NZ2019/050016 dated Aug. 27, 2020.
Melt Strength of Polypropylene: Its Relevance to Thermoforming. Lau et al., p. 2 (Year: 1998).
Machine Translation of JP 2002279822 A Description Jan. 4, 2023 (Year: 2001).

* cited by examiner

MEDICAL TUBES FOR BREATHING CIRCUIT

PRIORITY APPLICATIONS

The application is a continuation of U.S. application Ser. No. 16/970,510, filed Aug. 17, 2020, which claims priority to PCT Application No. PCT/NZ2019/050016, filed Feb. 22, 2019, which claims priority to U.S. Provisional Application No. 62/634,360, filed Feb. 23, 2018, each of which are incorporated herein by reference. Any and all applications for which a foreign or domestic priority claim is identified in the Application Data Sheet as filed with the present application are hereby incorporated by reference under 37 CFR 1.57.

BACKGROUND

Field

This disclosure relates generally to tubes suitable for medical use, and in particular, to medical tubes for use in a breathing circuit suitable for providing humidified gases to a patient and/or removing gases from a patient, such as in respiratory humidification systems.

Description

In breathing circuits, various components transport warm and/or humidified gases to and from patients. For example, medical tubes may be used in respiratory systems to convey respiratory gases between a respiratory component, such as a ventilator or a humidifier, and a patient. Respiratory gases can be heated and/or humidified prior to delivery to the patient to mimic the transformation of air that occurs as it enters the respiratory system. Heated medical tubes can deliver the heated and/or humidified respiratory gases directly to a patient interface or, in some cases, an additional medical tube can be located between the medical tube and the patient interface. Respiratory humidification can help reduce the likelihood of infection and/or tissue damage.

SUMMARY

Medical tubes can be used in breathing circuits or respiratory systems, for example, for delivering and/or removing humidified gases from a patient, such as in obstructive sleep apnea, neonatal, respiratory humidification, and surgical humidification systems including insufflation systems and systems for patients undergoing procedures under general anesthetic. The medical tubes described herein can include a substantially smooth bore formed by a bead and film.

In some examples, a medical tube for transporting gases can comprise a bead wrapped around a longitudinal axis of the medical tube. The bead can form a first portion of a lumen wall of the medical tube. The medical tube can also comprise a film wrapped around the longitudinal axis of the medical tube. A first portion of the film may overlie the bead and a second portion of the film may form a second portion of the lumen wall. The lumen wall, formed by the bead and the second portion of the film, can comprise a substantially smooth bore.

In some embodiments, the medical tube can include one or more of the following features, in any combination:

The bead can comprise a heating element. The heating element can comprise one or two or more heating wires disposed within the bead.

The bead can comprise at least one sensor wire for conveying power and/or data between at least one sensor and a controller. The at least one sensor wire can comprise one or two sensor wires disposed within the bead. The at least one sensor can comprise at least one of a temperature sensor, a humidity sensor, a flow sensor, and a pressure sensor.

The bead can comprise one or more ground or earth wires.

The bead can comprise a substantially flat surface forming the first portion of the lumen wall. The substantially flat surface of the bead can face an internal lumen of the medical tube. The second portion of the film can comprise a substantially flat surface forming the second portion of the lumen wall. The substantially flat surface of the film can face the internal lumen of the medical tube.

The film can comprise a plurality of layers. Each of the plurality of layers can comprise a winding of the film. A first layer of the plurality of layers can overlap a second layer of the plurality of layers over an outer surface of the bead to form an overlapping portion. The overlapping portion can overlie at least half of the outer surface of the bead. The overlapping portion can overlie between 55% and 95% of the outer surface of the bead. A first layer of the plurality of layers can overlap a second layer of the plurality of layers over an outer surface of a first winding of the bead and the first layer can also overlap a third layer of the plurality of layers over an outer surface of a second winding of the bead, the second winding adjacent to the first winding to form an overlapping portion. The overlapping portion can overlie at least half of the outer surface of each of the first winding of the bead and the second winding of the bead. The overlapping portion can overlie between 55% and 95% of the outer surface of each of the first winding of the bead and the second winding of the bead.

The first portion of the film can be fused to the bead.

The film can comprise a layered profile. An outer layer of the film can at least partially overlie an inner layer of the film.

The film can be between 0.1 mm and 1 mm thick. The film can be between 0.15 mm and 0.4 mm thick. an inner diameter of the substantially smooth bore of the medical tube can be between 1 mm and 30 mm.

The first and second layers of film may be fused together to form a single layer of the herein described thicknesses.

The medical tube can be capable of reprocessing.

The medical tube can be capable of cleaning and reuse for at least thirty, fifty, and/or one hundred cycles.

The medical tube can be autoclavable at a temperature of up to 140° C.

The bead can be spirally wrapped. The film can be spirally wrapped.

The film can be wound over the bead using force to push the film onto a mandrel via a roller such that the bead and the second portion of the film form the lumen wall with the substantially smooth bore.

The film can be wound over the bead using force to push the film onto a mandrel via a press such that the bead and the second portion of the film form the lumen wall with the substantially smooth bore.

The film can be wound over the bead using force to push the film onto a mandrel via blown gas or liquid such that the bead and the second portion of the film form the lumen wall with the substantially smooth bore.

The film can be wound over the bead and, via tension on the film from spinning a mandrel, the bead and the second portion of the film form the lumen wall with the substantially smooth bore.

The film can be wound over the bead using a vacuum with a perforated mandrel such that the bead and the second portion of the film form the lumen wall with the substantially smooth bore.

The film material can have a low melt strength such that, when wound over the bead, the film drapes down and naturally settles over the bead and mandrel such that the bead and the second portion of the film form the lumen wall with the substantially smooth bore.

The film can be wound over the bead by extruding the film as a shape to lay flat on the bead such that the bead and the second portion of the film form the lumen wall with the substantially smooth bore.

The bead can comprise a thermoplastic elastomer (TPE). The film can comprise a thermoplastic elastomer (TPE). The TPE can be polypropylene-based.

At least one of the bead and the film can be at least partially optically transparent.

The bead and/or the film can be colored for aesthetics or to indicate information to a user.

In some examples, a medical tube for transporting gases comprises a bead comprising a substantially flat surface. The bead can be positioned such that the substantially flat surface forms a first portion of a lumen wall of the medical tube. The medical tube also comprises a film, a first portion of the film laid over the bead and a second portion of the film forming a second portion of the lumen wall. The lumen wall, formed by the bead and the second portion of the film, can comprise a substantially smooth bore.

In some embodiments, the medical tube can include one or more of the following features, in any combination:

The first portion of the film can be bonded to the bead.

The film can comprise a layered profile. An outer layer of the film can at least partially overlies an inner layer of the film. An outer layer of the film can at least partially overlie an inner layer of the film over a peak of the bead opposite the lumen wall.

The second portion of the film can comprise a substantially flat surface forming the second portion of the lumen wall. The substantially flat surface of the bead and the substantially flat surface of the second portion of the film can be substantially aligned. The substantially flat surface of the bead and the substantially flat surface of the second portion of the film can be substantially parallel.

The bead and the film can be positioned so as to reduce a size of cavities formed between the bead and the film on the substantially smooth bore. Reducing the size of the cavities may reduce resistance to flow and potential dirt traps.

The film can be wound over the bead using force to push the film onto a mandrel via a roller such that the bead and the second portion of the film form the lumen wall with the substantially smooth bore.

The film can be wound over the bead using force to push the film onto a mandrel via a press such that the bead and the second portion of the film form the lumen wall with the substantially smooth bore.

The film can be wound over the bead using force to push the film onto a mandrel via blown gas or liquid such that the bead and the second portion of the film form the lumen wall with the substantially smooth bore.

The film can be wound over the bead and, via tension on the film from spinning a mandrel, the bead and the second portion of the film form the lumen wall with the substantially smooth bore.

The film can be positioned over the bead using a vacuum with a perforated mandrel such that the bead and the second portion of the film form the lumen wall with the substantially smooth bore.

The film material can have mechanical properties such that, when wound over the bead, the film drapes down and naturally settles over the bead and a mandrel such that the bead and the second portion of the film form the lumen wall with the substantially smooth bore.

The film can be positioned over the bead by extruding the film as a shape to lay flat on the bead such that the bead and the second portion of the film form the lumen wall with the substantially smooth bore.

A cross-section of the bead can be substantially D-shaped, triangular, square, trapezoidal, polygonal, or any other shape comprising at least one flat side.

A flat part of the cross section can be longitudinally aligned with the lumen wall and a semi-circular part of the cross section faces away from the lumen wall. The first portion of the film can be bonded or fused to the semi-circular part of the cross section.

The bead can comprise a heating element. The heating element can comprises one or two heating wires disposed within the bead.

The bead can comprise at least one sensor wire for conveying power and/or data between at least one sensor and a controller. The at least one sensor wire can comprise one or two or more sensor wires disposed within the bead. The at least one sensor can comprise at least one of a temperature sensor, a humidity sensor, a flow sensor, and a pressure sensor.

The bead can comprise one or more ground or earth wires.

The bead can be spirally wrapped. The film can be spirally wrapped.

The medical tube can include pneumatic connectors positioned on each end of the medical tube. The connectors can be overmolded onto each end of the medical tube. One or more of the connectors can include electrical connections for heater, sensor, or ground wires. One or more of the connectors can include one or more ports for sensors.

The medical tube can be capable of reprocessing.

The medical tube can be capable of cleaning and reuse for at least one hundred cycles.

The medical tube can be autoclavable at a temperature of up to 140° C.

The film can be between 0.1 mm and 1 mm thick. The film can be between 0.15 mm and 0.4 mm thick.

An inner diameter of the substantially smooth bore of the medical tube is between 1 mm and 30 mm.

The bead can comprise a thermoplastic elastomer (TPE). The film can comprise a thermoplastic elastomer (TPE). The TPE can be polypropylene-based.

The film can comprise a plurality of layers. Each of the plurality of layers can comprise a winding of the film. A first layer of the plurality of layers can overlap a second layer of the plurality of layers over an outer surface of the bead to form an overlapping portion. The overlapping portion can overlay at least half of the outer surface of the bead. The overlapping portion can overlay between 55% and 95% of the outer surface of the bead. A first layer of the plurality of layers can overlap a second layer of the plurality of layers over an outer surface of a first winding of the bead and the first layer can also overlap a third layer of the plurality of layers over an outer surface of a second winding of the bead, the second winding adjacent to the first winding to form an overlapping portion. The overlapping portion can overlay at least half of the outer surface of each of the first winding of the bead and the second winding of the bead. The overlapping portion can overlay between 55% and 95% of the each of the first winding of the bead and the second winding of the bead.

In some examples, any of the medical tubes described herein can include a first connector disposed at a first end of the medical tube and a second connector at a second end of the medical tube. The medical tubes can include one or more of the following features, in any combination:

In some embodiments, the first and second connectors are overmolded onto the medical tube.

In some embodiments, one or both of the first and second connectors are pneumatic connectors.

In some embodiments, one or both of the first and second connectors are tapered connectors.

In some embodiments, at least one of the first and second connectors includes a patient end sensor probe port.

In some embodiments, at least one of the first and second connectors includes an electrical connection. In some embodiments, the electrical connection comprises a port to connect heating and/or sensor wires. In some embodiments, the electrical connection comprises a pin. In some embodiments, the pin is solid. In some embodiments, the pin is rolled.

In some embodiments, at least one of the first and second connectors includes a sensor probe port that includes a locating depression or notch that is configured to mate with a locating tooth on a sensor probe housing to provide a predetermined location and orientation of a sensor of the sensor probe housing relative to a gases flow. In some embodiments, the sensor probe port further comprises a retention member configured to hold the sensor housing in place relative to the sensor probe port. In some embodiments, the retention member comprises a clip.

In some embodiments, a method for forming a medical tube, includes: wrapping a bead around a mandrel such that the bead is substantially flat where it contacts the mandrel at a first mandrel portion; and wrapping a film around the bead and the mandrel such that a first film portion overlies the bead and a second film portion contacts a second mandrel portion such that the second film portion forms a substantially flat surface.

In some embodiments, the method further comprises, in any combination:

Removing the mandrel such that the substantially flat portion of the bead and the substantially flat portion of the film form a substantially smooth bore of the medical tube.

Applying a force to the film via a roller such that the bead and the second portion of the film form the lumen wall with the substantially smooth bore.

Applying a force to the film via a press such that the bead and the second portion of the film form the lumen wall with the substantially smooth bore.

Applying a force to the film via a blown gas or liquid such that the bead and the second portion of the film form the lumen wall with the substantially smooth bore.

Wrapping the film may comprise: applying tension to the film; and spinning the mandrel such that the bead and the second portion of the film form the lumen wall with the substantially smooth bore.

In some embodiments, the mandrel is perforated and the method further comprises applying a vacuum with the perforated mandrel such that the bead and the second portion of the film form the lumen wall with the substantially smooth bore.

In some embodiments, the method further comprises heating the film such that the film to drapes down and naturally settles over the bead such that the bead and the second portion of the film form the lumen wall with the substantially smooth bore.

In some embodiments, the method further comprises positioning the film over the bead by extruding the film as a shape to lay flat on the bead such that the bead and the second portion of the film form the lumen wall with the substantially smooth bore.

In some examples, a breathing circuit kit can include a medical tube as described herein and at least one of: a dry line, a chamber, an expiratory tube, a y (wye) piece, an adapter, a sensor, a patient interface, and a least one water trap. The expiratory tube can be breathable. The expiratory tube can be non-breathable. In some examples:

The kit comprises the medical tube, the expiratory tube, the y (wye) piece, and the chamber.

The kit comprises the medical tube, the expiratory tube, the y (wye) piece, and the patient interface.

The kit comprises the medical tube, the expiratory tube, the y (wye) piece, the chamber, and the water trap.

In some examples, a breathing circuit kit can include an inspiratory tube, an expiratory tube, and/or a dry line. One or more of the inspiratory tube, the expiratory tube, and/or the dry line can be configured as any of the medical tubes described above or herein.

In some embodiments, the kit may further comprise at least one of, or any combination of, a chamber, a y (wye) piece, an adapter, a sensor, a patient interface, and a water trap. In some embodiments, the expiratory tube is breathable. In some embodiments, the expiratory tube is non-breathable.

In some examples, a breathing circuit system includes a medical tube as described herein, a patient interface connected to a first end of the medical tube, and a humidifier and/or a flow generator connected to a second end of the medical tube.

These medical tubes, which can include a substantially smooth bore, can provide one or more advantages. For example, in some embodiments, medical tubes with a smooth bore may advantageously have a lower resistance to flow (RTF) than a conduit with comparable dimensions having a non-substantially smooth (e.g., corrugated) bore. Thus, in some embodiments, the smooth bore medical tubes described herein may provide improved performance, efficiency, and flow as compared to other medical tubes. As another example, some of the medical tubes described herein are configured such that they are reusable. That is, some of the medical tubes can be configured to be suitable for reprocessing. As another example, some of the medical tubes described herein are configured to be reusable for hundreds of cycles.

These and other features and advantages of this disclosure will become more fully apparent from the following figures and detailed description. This summary is provided to summarize some features of the invention(s) and should not be construed as limiting.

BRIEF DESCRIPTION OF THE DRAWINGS

Certain features, aspects, and advantages of the present disclosure will now be described with reference to the drawings. The drawings and the associated descriptions are provided to illustrate certain features, aspects, and advantages of the present disclosure and not to limit the scope of the disclosure.

DETAILED DESCRIPTION

Figure 1:
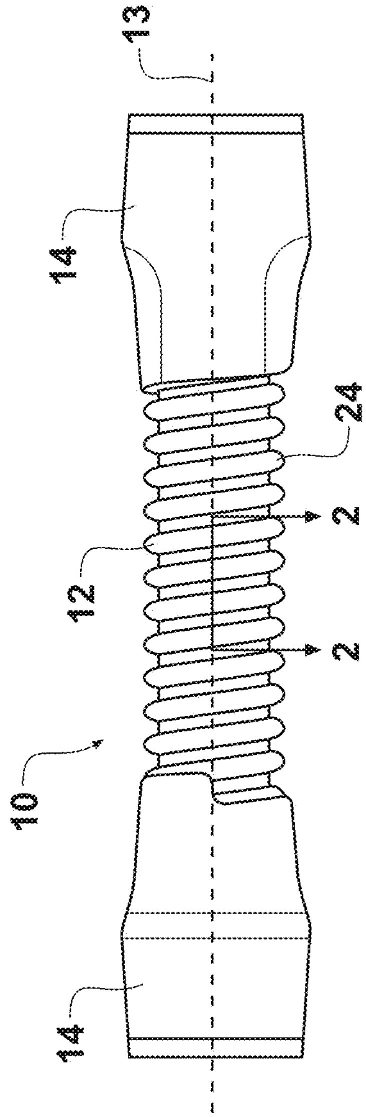
FIG. 1 is a top view of an embodiment of a medical tube.

This application relates to medical tubes for use in breathing circuits or respiratory systems. The medical tubes may be used for delivering and/or removing humidified gases from a patient, such as in obstructive sleep apnea, neonatal, respiratory humidification, and surgical humidification systems including insufflation systems and systems for patients undergoing procedures under general anesthetic. The medical tubes can be used to deliver gases between a component, such as a humidifier, and a patient, or between two components of a breathing circuit or respiratory system. In some embodiments, the medical tubes can be inspiratory tubes, expiratory tubes, patient interface tubes, supply tubes, dry lines, insufflation tubes, etc.

As will be more fully described below, the medical tubes described herein can include a substantially smooth bore (or a substantially smooth inner wall or lumen) that is formed by a bead and film (or tape). The bead can be helically wrapped to form a portion of the substantially smooth bore, and the film can be wrapped over the bead such that a portion of the film overlies the bead and another portion of the film forms another portion of the substantially smooth bore.

The term “smooth bore” is used herein broadly to describe a substantially smooth inner surface of a lumen extending through the medical tube. In some instances, the term smooth bore can describe a tube that does not have substantial repeating inner surface features (e.g., tubes that have inner surfaces that are not corrugated, wavy, ridged, etc.). In some instances, the term smooth bore can describe a tube wherein pockets (or cavities, recesses, indentions, etc.) within the tube are minimized, reduced, or eliminated entirely. In some instances, the term smooth bore can describe a tube wherein inner surfaces of the bead and the film are substantially aligned and/or collinear. One of skill in the art would appreciate that tubes made of multiple materials, or wrapped materials laid at different times, may experience some variation on their inner surfaces. Such minor manufacturing variations, even if repeating, are intended to be encompassed by the term substantially smooth bore.

Medical tubes that include a smooth bore may not substantially disturb (or may decrease disturbances) of a generally laminar flow of gases through the passageway or lumen defined by the smooth bore. Increasing the smoothness of the bore can decrease turbulence and create a more parabolic wave front across the inner wall of the lumen. A smooth bore tube may also provide no pockets in which vapor or gases could be trapped or in which condensate or other liquids might pool, as a corrugated tube would have. The vapor carried by the gases is therefore encouraged to exit the tube and thus be delivered to the patient. In some embodiments, medical tubes with a smooth bore may advantageously cause the conduit to have a lower resistance to flow (RTF) than a conduit with comparable dimensions having a non-substantially smooth (e.g., corrugated) bore. Thus, in some embodiments, the smooth bore medical tubes described herein may provide improved performance, efficiency, and/or flow as compared to other medical tubes.

In another aspect, some of the medical tubes described herein are configured such that they are reusable. That is, some of the medical tubes can be configured to be suitable for reprocessing. “Reprocessing” refers to processes of cleaning, disinfecting, and sterilizing such that the medical tube is suitable for re-use. The smooth bore discussed above also provides added benefits in terms of the reusability and reprocessability of the medical tubes. As mentioned, the smooth bore can provide the benefit of reducing the trapping of vapor, condensates, and other liquids or gases. This can improve cleanability/reprocessing as the smooth internal surface means there are fewer or no cavities (or smaller cavities) for dirt, germs, bacteria, bodily fluids, or other things to be removed during cleaning to accrue.

Reusability of tubes in respiratory therapy can be important as it minimizes tube replacement. This can increase simplicity and decrease cost of certain respiratory systems and breathing circuits. Many existing reusable tubes have limitations. For example, certain existing tubes can only be cleaned through pasteurization at temperatures that do not exceed 75° C. Temperatures above 75° C. can damage the tubes. At these temperatures (below 75° C.), pasteurization and cleaning is a long and slow process. Alternatively, certain reusable tubes can require cleaning with harsh chemicals that can be expensive and undesirable to handle or work with. When using these methods, known tubes last approximately 25 cycles until they need to be replaced due to functional deterioration or degradation.

Advantageously, some of the medical tubes described herein are configured to be reusable for up to hundreds of cycles. For example, certain of the medical tubes described herein have been tested for between 100 and 200 cycles. Thus, the medical tubes described herein can provide an improved lifespan over known medical tubes. The medical tube can be capable of cleaning and reuse for at least thirty, fifty, and/or one hundred cycles. Further, some of the medical tubes described herein are configured to be reprocessed at temperatures higher than 75° C. For example, the medical tubes can be autoclavable at a temperature of around 121° C. or 134° C. In some embodiments the medical tubes can be autoclavable at a temperature of up to 140° C., such as 80° C., 90° C., 100° C., 110° C., 120° C., 130° C., or 140° C. Thus, these medical tubes can be reprocessed more quickly than known tubes. Such reprocessing may not require the use of chemicals (e.g., the harsh chemicals discussed above).

These and other features and advantages of the medical tubes of the present disclosure will now be described in greater detail with reference to the figures. The drawings illustrate only certain embodiments provided to illustrate the principles discussed herein and should not be construed as limiting this disclosure.

Medical Tubes

Figure 6:
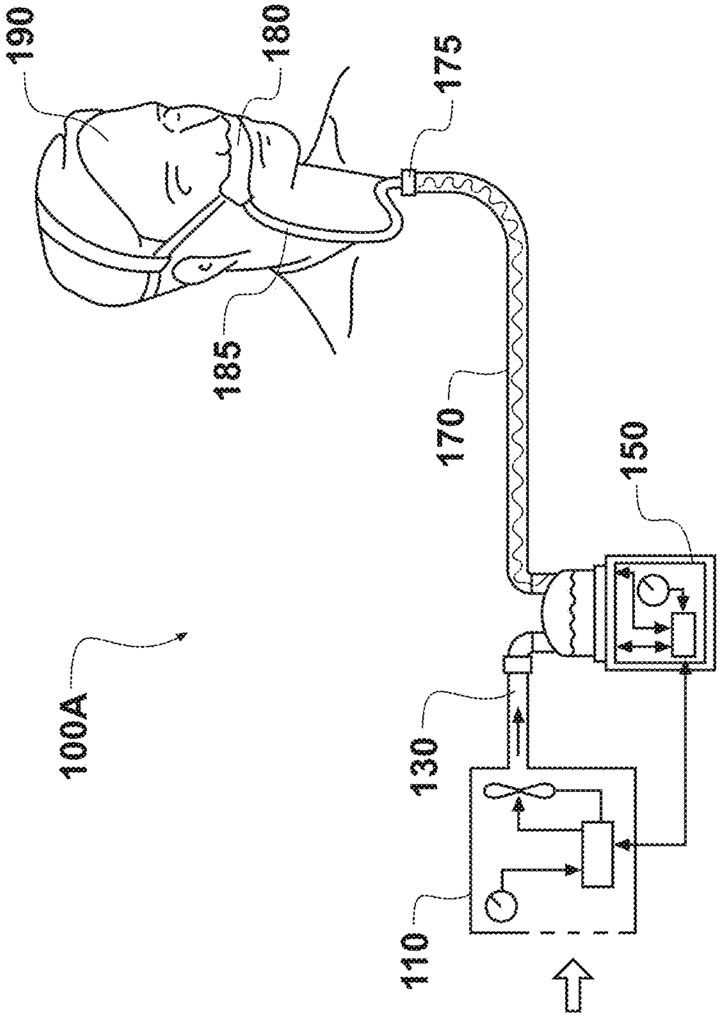
FIG. 6 a schematic illustration of an embodiment of breathing circuit including an inspiratory medical tube and a humidifier.
Figure 7:
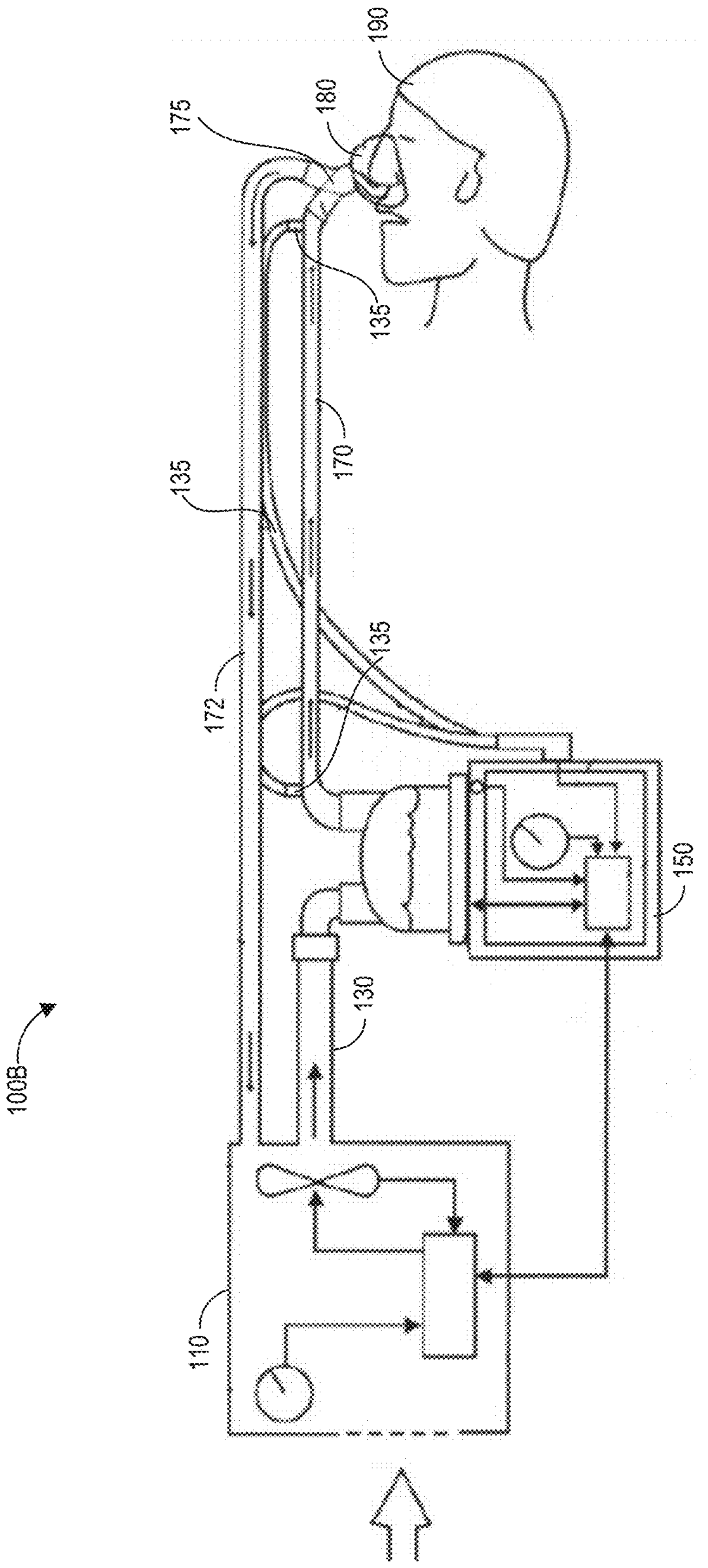
FIG. 7 a schematic illustration of an embodiment of breathing circuit including an inspiratory medical tube, an expiratory medical tube, and a humidifier.

FIG. 1 is a top view of an embodiment of a medical tube 10. In the illustrated embodiment, the tube 10 comprises a tube body 12 extending along a longitudinal axis 13 between connectors 14 located on both ends of the tube body 12. The tube body 12 can define a substantially smooth bore (a substantially smooth inner surface) that extends through the tube 10 to carry, for example, gases. The connectors 14 can be pneumatic connectors configured to allow a pneumatic connection to other components in a breathing circuit or respiratory system. Example breathing circuits and respiratory systems are shown in FIGS. 6 and 7, which are described below. Other types of connectors 14 can also be used.

In some embodiments, the tube body 12 is flexible such that the medical tube 10 can bend into various desired configurations and permit patient movement. In some embodiments, a cross-section of the tube body 12 is generally or substantially circular, such that the tube body 12 comprises a hollow cylindrical shape. In other embodiments, the tube body 12 can comprise other cross-sectional shapes, such as oval or polygonal shapes. The structure of the tube body 12 will now be described in greater detail with reference to FIG. 2.

Figure 2:
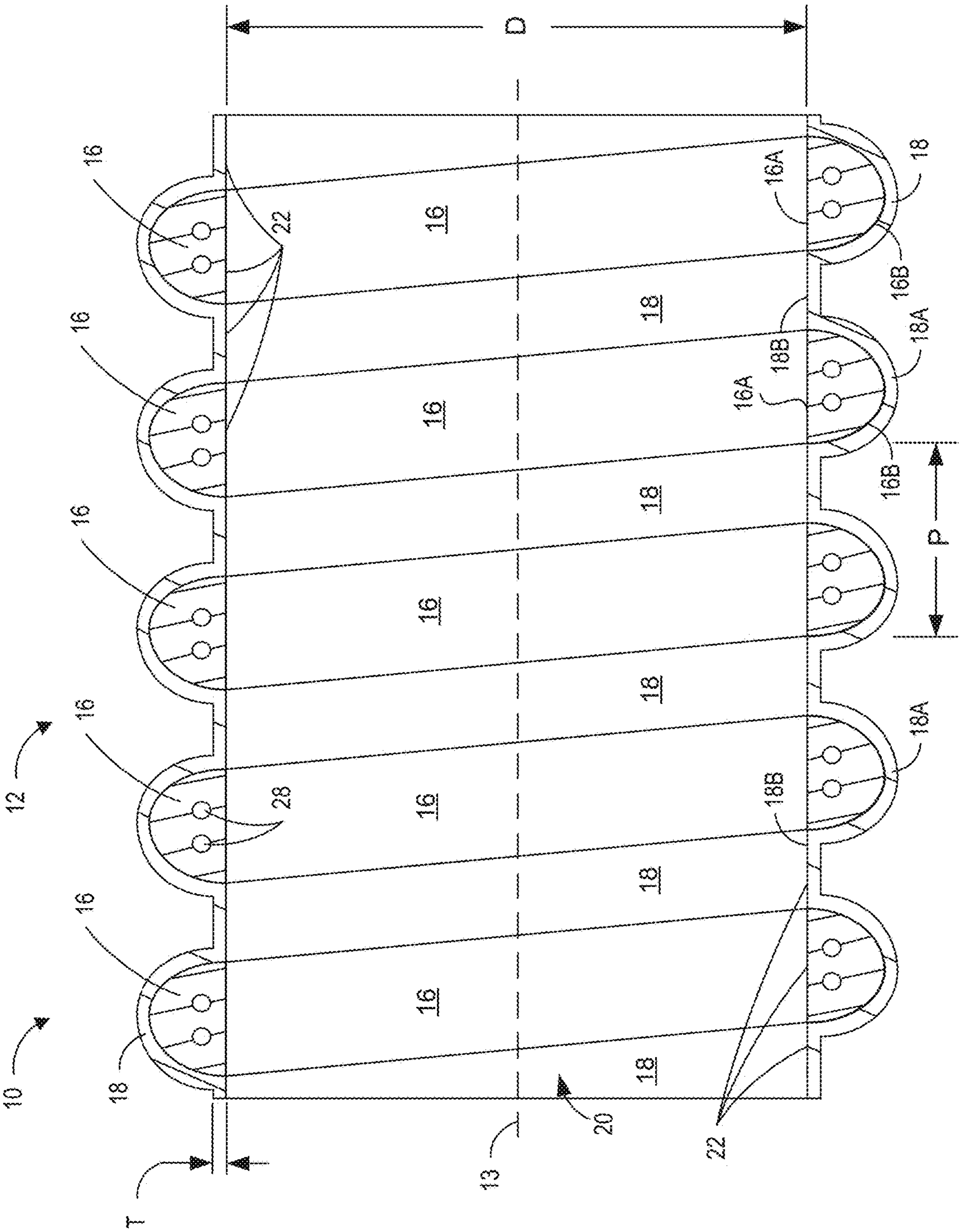
FIG. 2 is a cross-sectional view of a portion of the medical tube taken along the line 13 shown in FIG. 1.

FIG. 2 is a cross-sectional view of a portion of the medical tube 10 taken along the line 13 shown in FIG. 1 and illustrates a portion of the tube body 12. As illustrated, the tube body 12 of the medical tube 10 can be formed from a bead 16 and tape or film 18. As will be described in greater detail, the bead 16 and the film 18 can define a bore (or inner lumen) 20 of the medical tube 10. An inner surface 22 of the medical tube 10 may at least partially define the bore 20. The inner surface 22 can be substantially smooth. Thus, the bore 20 can be considered (and is often referred to herein as) a substantially smooth bore. As will be described in greater detail below, the inner surface 22 can comprise alternating portions of the bead 16 and the tape or film 18. For example, as illustrated in FIG. 2, the inner surface 22 can comprise portions 16A of the bead 16 and portions 18B of the film 18. The portions 16A of the bead 16 and the portions 18B of the film 18 can be substantially flat as described below. It should be appreciated by one of skill in the art that the bead, which may be much thicker and/or made of a harder or more rigid material than the film may impart structural support, reinforcement, and/or resistance to crushing to the more flexible film portions of the tube. Such structural support, reinforcement, and/or resistance to crushing may be important in medical tubes, and in particular for breathing tubes, which must meet international standards defining usage characteristics and parameters.

Forming the inner surface 22 and the bore 20 in this manner (with alternating portions of the bead 16 and the film 18) can be achieved, in some embodiments, by helically winding bead 16 with space between each winding, and then providing the film 18 over the helically wound bead 16 such that at least a first portion of the film 18 (e.g., the portion 18A) is disposed over at least one winding of the bead 16 and a second portion of the film 18 (e.g., the portion 18B) is positioned between the wraps of the bead 16. In this configuration, the smooth bore 20 (and inner surface 22) can be formed by alternating portions of the bead 16 and the film 18.

In some embodiments, the film 18 comprises an elongate strip that is helically wound over the bead 16. The total thickness of the film 18 (i.e., the combined thickness of any and all layers of the film 18, if multiple layers are present) may have a thickness T as shown. In some embodiments, the thickness T is between 0.1 mm and 1 mm. In some embodiments, the thickness T is between 0.15 mm and 0.4 mm. Other thicknesses T, both larger and smaller than the listed values may also be used. In an embodiment where the film 18 comprises a plurality of layers of film, where the layers are overlapped, there may be a locally larger thickness than where they are not overlapped. The film 18 can be made from thermoplastic polymer (TPE) material. In some embodiments, the TPE material is polypropylene-based. In another example embodiment, the film can be made of the same material, or the same family of material as the bead 16. In some embodiments, the film 18 may be at least partially optically translucent to enable a user to see condensate or other material within the lumen.

Additional detail regarding methods for manufacturing the medical tube 10 is provided below with reference to FIGS. 3A-4. Further, the substantially smooth inner surface 22 (formed by alternating portions 16A of the bead 16 and portions 18*b* of the film 18) can be achieved by configuring the bead 16 and the film 18 such that each includes a substantially flat portion. The substantially flat portions of the bead 16 and the film 18 can be aligned to form the substantially flat inner surface 22 of the substantially smooth bore 20.

As mentioned above, a substantially smooth bore 20 can provide one or more advantages. For example, a smooth bore 20 can reduce the resistance to flow (RTF) of the medical tube 10. This can permit or allow for a reduction in the diameter or cross-sectional area of the medical tube 10, while maintaining an acceptable resistance to flow. This reduction in diameter or cross-sectional area of the medical tube 10 can also reduce the compressible volume of the medical tube 10. This can reduce the compressible volume of at least a portion of a breathing circuit or respiratory system into which the medical tube 10 is integrated, which can reduce the potential for error in delivered tidal volume. A ventilator typically intends to deliver a set volume of gas to the patient (a 'tidal volume') for each breath. Reducing the error in delivered tidal volume can advantageously ensure that the patient is receiving the correct gas volume.

It has been discovered that, if the increased RTF resulting from decreasing the tube's internal diameter is outweighed by the decrease in RTF resulting from using a smooth bore, then there is a net decrease in RTF in a breathing circuit or at least net decrease in RTF in the medical tube. The smooth bore of the medical tube lowers the RTF, which allows for the reduction of the diameter of which would normally increase the RTF, wherein the smoothness of the bore and the reduction in diameter can be balanced. As described herein, the reduction in the diameter or cross-sectional area can reduce the compressible volume. This lowering of the compressible volume of the inspiratory tube can offset an increase of the compressible volume of the expiratory tube, such as by increasing the diameter or cross-sectional area of the expiratory tube. Increasing the diameter or cross-sectional area of the expiratory tube can create a greater surface area of the expiratory tube, which, for non-water vapor permeable tubes with water traps, can allow for better cooling of the gases causing more rainout in the expiratory tube, and less damaging water vapor being delivered back to the ventilator. For vapor permeable expiratory tubes, increasing the diameter or cross-sectional area of the expiratory tube can create a greater surface area of the expiratory tube which increases the vapor permeability of the expiratory tube and advantageously decreases the amount of damaging water vapor being delivered back to the ventilator.

The use of a smooth bore may also have the added benefit of providing no, fewer, or lesser pockets in which vapor can be trapped or condensate or other substances might pool, as a corrugated tube would have. The vapor carried by the gases is therefore encouraged to exit the tube and thus be delivered to the patient. Further, the smooth bore can contribute to the cleanability, reprocessability, and reusability of the medical tube.

The cross sectional shape of the bead 16 may be any that maintains a substantially smooth bore 20 along the inner surface 22. In general, this may be any shape that includes at least one flat inner side, such as triangular, square, trapezoidal, semi-circular, quadrilateral, or other polygonal shapes. In the illustrated embodiment, the bead 16 comprises a substantially or generally D-shaped cross-section. The D-shaped cross-section can include the substantially flat portion 16A and a curved portion 16B. The substantially flat portion 16A can define a portion of the substantially smooth bore 20. The substantially flat portion 16A can face toward the inner lumen and the longitudinal axis 13. The curved portion 16B can extend generally away from the inner lumen and the longitudinal axis 13. Although covered by the film 18, the curved portion 16B can form a helical ridge 24 on the exterior surface of the tube body 12 as shown in FIG. 1.

In some embodiments, the shape of the bead 16 can improve the crush resistance and/or recovery of the medical tube 10. For example, the curved portion 16B can provide an unstable surface, which can be better at absorbing or diverting crush forces. Thus, during the application of reasonable force, adjacent wraps or windings of the bead 16 can roll or lean sideways, resisting crushing, rather than collapsing downward in a way that may allow crushing of the medical tube 10. This may reduce restriction of the lumen or bore 20 of the medical tube 10 and ensure that some flow can be maintained through the medical tube 10. Once the force ceases and/or is removed, the medical tube 10 can recover well and quickly. Thus, the medical tube 10 can regain its original shape with little or no impact on the medical tube 10.

In some embodiments, the rolling or leaning feature of medical tube 10 can depend on the pitch P at which the bead 16 is helically wound (i.e., distance between successive wraps from the start of one winding to the start of the next). In some embodiments, the pitch 26 is between 2-20 mm.

Further, in some embodiments, the shape of the bead 16 can provide a bonding region for the film 18. For example, the film 18 can bond or fuse along the outer or curved portion 16B. This can improve the flexibility and/or tensile strength of the medical tube 10 by allowing the film 18 to extend to a maximal length between adjacent windings of the bead 16. The bonding can also reduce the susceptibility of the medical tube 10 to manufacturing variation, which can make the medical tube 10 more resilient. In some embodiments, the film 18 can bond over a smaller region of the shape or can bond over a larger region of the shape than is illustrated in FIG. 2.

The bore 20 of the medical tube 10 may have an inner diameter D as shown. In some embodiments, the inner diameter D is between 1 mm and 30 mm. Other diameters, both larger and smaller are also possible.

Because the bead 16 forms part of the inner surface 22 that defines the bore 20, the bead 16 can be considered a structural component of the bore 20. For example, the bead 16 can provide strength and rigidity to the bore 20 and the medical tube 10 overall.

As mentioned above, the bead 16 can be made from thermoplastic polymer (TPE) material. In some embodiments, the TPE material is polypropylene-based. In another example embodiment, the bead can be made of the same material, or the same family of material as the film 18. The bead 16 may, in some embodiments, be partially optically translucent to enable a user to see condensate or other material within the lumen. The bead 16 may be colored to indicate sizing the tube, to designate whether the tube includes heating and/or sensing wires, to designate which circuit component (inspiratory or expiratory) the tube is, and/or for aesthetics. For instance, in one embodiment, the bead 16 is blue, or light blue. The blue color may indicate that the tube is for inspiratory use. In another embodiment, the bead 16 is grey or light grey. The grey color may indicate that the tube is for expiratory use.

As shown in FIG. 2, in some embodiments, various components can be embedded within the bead 16. For example, in the illustrated embodiment, a heating element, comprising, preferably, two heating wires 28, is disposed within the bead 16. In some embodiments, the two heating wires 28 may comprises a single wire that extends from one end of the tube to the other end of the tube and then is doubled back such that both ends of the heating wire can be attached to a single connection point on one end of the tube. In some embodiments, the heating element may comprise a single heating wire or greater than two heating wires. In some embodiments, other components, such as one or more sensing and/or ground or earth wires may also be disposed within the bead 16. Sensor wire(s) embedded within the bead 16 can be configured to measure, for example, temperature, pressure, flow, or humidity. Such heating and/or sensing/ground wires may be any suitable size considering the overall bead size. In one embodiment, the wires are in the range of 0.05-1.0 mm, 0.1-0.8 mm, 0.1-0.4 mm. Overall, there may be one, two, three, four or more wires within the bead 16, for heating and/or sensing/ground or earth functions. In another embodiment, the wires are wound in a pattern or laid through the lumen of the tube, rather than being embedded or encapsulated in the bead. In such an embodiment, the wires may be held in place at one or both ends.

Because the bead 16 forms a portion of the inner surface 22 that defines the bore, the heating element 28 is positioned in close proximity to gases within the medical tube 10. Positioning one or more heating elements 28 within the bead 16 of the tube 10 can maximize humidification, minimize condensate formation, maintain the condition of the gases, and contribute to the efficiency of the tube 10 and/or any associated breathing circuit or the humidification system. Advantageously, locating the wires in the bead (rather than in the lumen) reduces the resistance to flow of the tube. In some embodiments, the heating elements 28 (and/or other sensor/ground or earth wires) can be similarly embedded or positioned within the film 18. It should further be appreciated by one of skill in the art that the benefit of two relatively small wires (relative to the size of the bead) located in the portion of the bead close to the inner surface of the tube wall (as shown in the Figures) is that this can be an efficient way to heat the gas flowing through the tube, while reducing the risk of unacceptably high temperatures on the outer surface of the tube wall. International standards for breathing circuits govern the maximum outer surface temperature to limit the risk of burning a patient or carer. Accordingly, in some embodiments, the primary purpose of such heater wires is not for reinforcement, but for maintaining water in (or re-evaporating water to) a vapor state in the tube and reducing the risk that such vapor condenses into (or stays condensed as) liquid water and causes damage to the patient or other equipment. Moreover, in some embodiments a pair or pairs of wires are preferable (as compared to a single wire), especially in a medical tube as described herein, to provide for a length of wire doubled back along the length of the tube to a single connection point to a power supply/ground. This can be seen, for example, in at least the embodiments of FIGS. 2, 3A-B, 4A-B, and 5A-C. The single connection point offers costs savings, reliability, functionality, and usability benefits over other design, including designs that include wires or the like for reinforcement purposes.

As shown in FIG. 2 and mentioned above, the inner surface 22 that defines the bore 20 is substantially smooth. This can be achieved by minimizing or eliminating any gaps or pockets formed between the film 18 and the bead 16 at the inner surface 22. Generally, the inner surface 22 is formed by substantially flat portions of the bead 16 and substantially flat portions of the film 18 that are aligned as shown.

Several example manufacturing processes that can be used to form the medical tube 10 with the substantially smooth bore 20 will now be described with reference to FIGS. 3A-3B. In some embodiments, these manufacturing processes involve helically winding the bead 16, and then helically winding the film 18 over the bead 16. In some embodiments, the bead 16 is first helically wrapped over a mandrel, and then the film 18 is helically wrapped over the mandrel and the bead 16.

Figure 3A:
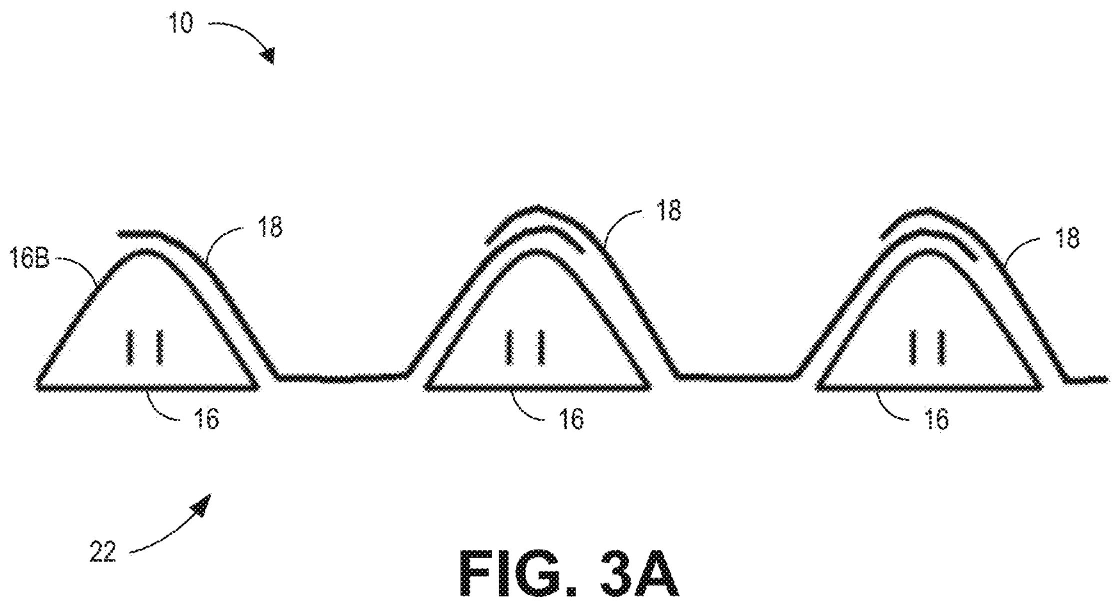
FIG. 3A is a detailed view of a portion of a wall of the medical tube of FIG. 1, illustrating an embodiment of an intermediate depiction of film of the medical tube positioned over a bead of the medical tube.

FIG. 3A is a detailed view of a portion of a wall or inner surface 22 of the medical tube 10 and illustrates an embodiment of an intermediate depiction of the film 18 positioned over the bead 16 during a manufacturing process. As shown, the film 18 may comprise multiple layers. The layers may be formed by individual strips of film 18 or by winding the film 18 such that subsequent windings are positioned over top of previous windings. As shown, the film 18 is positioned over the bead 16 as well as in the flat depressions between successive windings of the bead 16. Further, FIG. 3A illustrates that in some embodiments, layers of the film 18 may overlap over the peaks of the beads 16. In some embodiments, overlap of layers of the film 18 may occur in other areas or not at all.

In one example embodiment, each layer (e.g., each winding) of film 18 overlays at least half of the outer bead surface 16B. In another example embodiment, each layer of film 18 overlays more than half of the outer bead surface 16B. In a further example embodiment, each layer of film 18 overlays between 55-95% of the outer bead surface 16B. In some embodiments, each layer of film 18 overlays at least a portion of two adjacent bead windings. For example, in one embodiment, each layer of film 18 overlays at least half of the outer bead surface 16B of two adjacent bead windings. In another example embodiment, each layer of film 18 overlays more than half of the outer bead surface 16B of two adjacent bead windings. In a further example embodiment, each layer of film overlays between 55-95% of the outer bead surface 16B of two adjacent bead windings. In these embodiments, the film 18 may be locally thicker over the beads 16 due to the overlap and locally thinner in the areas between the beads 16. In some embodiments, these thicker parts can ensure a strong film bond to the bead 16. Additional benefits of the thicker regions may include some leniency in the tube surface temperature (e.g., it may help lower the tube surface temperature where it is thicker), increased tensile strength of the tube, and decreased potential for dirt gathering on the outer side of the tube where film meets. In some embodiments, layers of film 18 may be positioned to overlap in the regions between bead windings. In some embodiments, successive layers of overlapping film 18 can be bonded or fused by heat; however, glue or chemical bonding agents may be used.

Figure 3B:
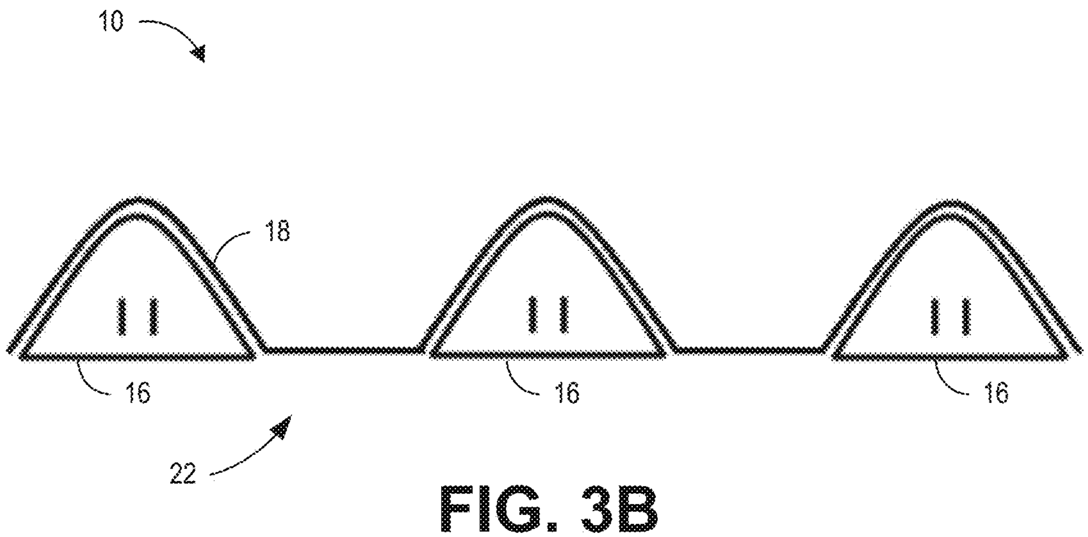
FIG. 3B is a detailed view of the portion of the wall of the medical tube of FIG. 3A, illustrating an embodiment of an assembled state of the film and the bead of the medical tube.

FIG. 3B is a detailed view of the portion of the wall or inner surface 22 of the medical tube 10 and illustrates an embodiment of an assembled state of the film 18 and the bead 16 of the medical tube 10. As shown, the layers of film 18 may be bonded or fused together (such that layers of film are not readily distinguishable from each other), and the film 18 can be bonded to the bead 16. The wall 22 comprises a substantially flat surface 22 made of the flat portions of the bead 16 as well as the portions of the film 18 positioned between the windings of the bead 16. In FIGS. 3A and 3B, gaps are schematically exaggerated between the layers of film 18 and the bead 16 for illustration. As discussed above, the film 18 may be thicker at the overlapping regions (e.g., the peaks of the bead 16) even though this is not shown in FIG. 3B.

Medical tube 10 may be manufactured according to various methods. For example, the medical tube 10 can be manufactured by using force to push the film 18 onto the bead 16 and/or into the spaces between successive windings of bead 16 via a roller or press, or from a blown gas or fluid; via tension from spinning the mandrel at a speed that causes the film 18 to press or be pulled tightly down onto the mandrel and form the flat surfaces; using a vacuum with a perforated mandrel to suction the film to the mandrel; utilizing a film 18 with material properties selected to cause the film 18 to naturally drape down and settle over the bead and mandrel to create the flat surfaces; the application of heat and/or chemicals to the bead 16, film 18, and/or mandrel; and/or extruding the film 18 as a shape configured to lay flat on the bead 16 and mandrel. Alternatively or in addition to such mechanical manufacturing methods, the tube may undergo post-processing following winding, including treatments such as ultrasonic bonding, heating (direct and/or infrared), or the application of heat and/or chemicals. These and other possible manufacturing processes can push or pull the film 18 into contact with the bead 16 and into the depressions between successive bead windings, thereby minimizing and lessening any gaps from forming between the bead 16 and the film 18 and creating the substantially smooth bore 20.

In some embodiments, after the bead 16 and film 18 are wound together to form the medical tube 10, the bead 16 and the film 18 can be fused or bonded together. For example, in some embodiments, ultrasonic bonding, heating (direct or infrared), glue, chemical bonding, or other fusing or bonding methods are applied post processing after winding to join the bead 16 and film 18. In some embodiments, in this assembled state, the medical tube 10 can be sufficiently durable so as to be reusable and reprocessable as described herein. It should be appreciated by one of skill in the art that although chemical methods have been disclosed and may be used to bond the film to the bead or to bond the film to another layer of film, in the medical and breathing tube field and for the medical tubes described herein, it can be preferable to use heat bonding methods as are known in the art and disclosed herein, where possible. This is because the heat bond may be more robust and resistant to separation, because use of bonding chemicals may limit the available methods to clean and reprocess the tube, because use of chemicals may require extra safety and international standards compliance testing, approval, and/or warnings, and the like, which may not be of relevance in non-breathing tube fields. Each of these possible consequences adds cost and decreases usability and reliability for a chemical-substance bonded tube, such as a solvent-bonded tube.

As noted, the manufacturing process leads to the formation of flat regions intermediate and adjacent to the bead windings. This means that the film 18 is tight to the bead 16, which may stop the accrual of bacteria and dirt that would otherwise occur if gaps were present. Stopping the formation and build-up of bacteria may help to improve the longevity/reusability of the tube 10, and may decrease the risk of cross-infection between successive patient users.

As shown in FIG. 1, the medical tube 10 may comprise connectors 14 for connecting the tube 10 to other components in a breathing circuit or respiratory system. The connectors 14 can be overmolded onto the tube body 12, or may be attached in any other suitable manner, such as by friction fit, interference fit, being threaded into place, clipped, glued, or otherwise held. For example, in some embodiments, after the tube body 12 is formed (as described above), connectors 14 can be molded directly onto each end. The connectors 14 can include connection points that allow the medical tube 10 to be connected (e.g., pneumatically connected) to other components in a breathing circuit or respiratory system (e.g., such that gases can be conducted through the medical tube 10). Those of skill in the art will appreciate that the size and the shape of the connectors 14 can be varied and additional features may be included for connection to various different components. All of these variations are intended to be within the scope of this disclosure. The connectors 14 can comprise tapered connectors. In a further example embodiment, the molded material of the connectors may be the same material and/or the same family of material as the bead 16 and/or film 18. As would be appreciated by one of skill in the art, selecting an connector overmold material that is the same as or in the same family as the bead and/or film material may advantageously allow for easier or more durable bonding between the connector overmold and the tube wall.

FIGS. 4A-5C illustrate embodiments of medical tubes 10 that include connectors 14 with additional features. For example, in addition to making the pneumatic connections described above, the connectors 14 may include additional features for establishing an electrical connection to the heating wire(s), sensor wire(s), grounding wire(s), etc., that are formed into the medical tube 10. In some embodiments, as described below (with reference to FIGS. 6A-6C), the connectors 14 can also include ports for inserting or locating one or more sensors.

Figure 4A:
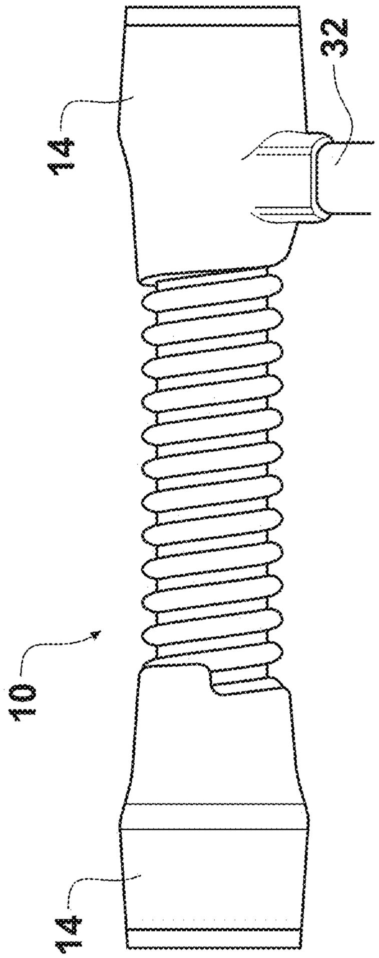
FIG. 4A is a top view of an embodiment of a medical tube including connectors at each end, with one of the connectors including an embodiment of an electrical connection.
Figure 4B:
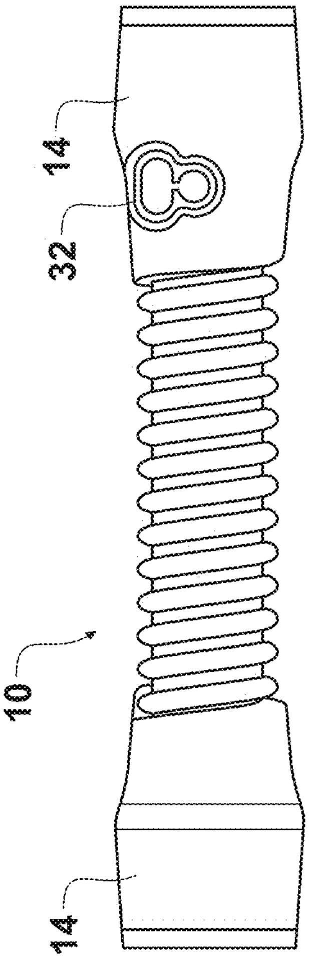
FIG. 4B is a side view of the medical tube of FIG. 4A.

FIGS. 4A and 4B are a top and side views, respectively, of an embodiment of the medical tube 10 including connectors 14 at each end. As before, the connectors 14 can be overmolded onto the tube body 16 (or attached in various other manners, as described above) and can establish pneumatic connections to the medical tube 10. For example, the connectors 14 can be overmolded onto the tube body 16 as described in U.S. patent application Ser. No. 14/115,806, filed on Mar. 3, 2014, which is scheduled to issue on Feb. 26, 2019, as U.S. Pat. No. 10,213,571, and which is incorporated herein by reference in its entirety.

As one example, a method for overmolding the connectors 14 on the medical tube 10 may comprise providing a length of tube (which can be formed as described above of the bead 16 and the film 18), locating one or more first pre-formed component or components substantially adjacent to and/or slightly overlapping at least one of the ends of the tube, locating one or more second pre-formed component or components substantially at or adjacent to and/or slightly overlapping the at least one end of the tube, and, in a single over-molding procedure, over-molding a cuff about the first pre-formed component(s) and second pre-formed component(s) and about at least a portion of the at least one end of the tube wall. The over-molded cuff can attach to and locate the pre-molded component(s) in place relative to the at least one end of the tube. In some embodiments, the first and/or second pre-formed component is a pneumatic port, the pneumatic port providing for pneumatic connection with the at least one end of the medical tube. In some embodiments, the first and sometimes second pre-formed components may be positioned so as to be spaced from or overlapping with the tube wall. The over-molded cuff may comprise a contoured external surface for gripping by a user. The first and/or second pre-formed components may in some embodiments include the ports or connections described herein (such as for locating sensors, making electrical connections, and/or making pneumatic connections.

It should be appreciated by one of skill in the art that overmolding connectors in this way allows for a smooth and unbroken surface between the terminal end of the pneumatic connector and the tube wall, which advantageously reduces dirt-traps, allows for more effective and easier reprocessability (as discussed herein, and especially in concert with a tube having a smooth inner bore), and is a robust design which can weather repeated handling and reprocessing without leakage or breakage. In some embodiments, and as shown in FIGS. 4A and 4B, for example, a first end of the connector 14 can overlap the tube body 12 and directly contact the film 18. A portion of the first end of the connector 14 can be aligned with the bead 16 along a helical portion of the tube body 12 and can comprise an edge offset by the bead pitch distance.

In the illustrated embodiment, one of the connectors 14 includes an embodiment of an electrical connection 32. The electrical connection 32 may be any suitable shape or form. In one embodiment, the electrical connection is in the shape of a cloverleaf. In some embodiments, the electrical connection 32 is positioned on the connector 14 on the chamber end (e.g., humidifier end) of the medical tube 10. The electrical connection 32 may comprise a port to connect heating wires (e.g., heating element 22). The heating wire pins in the electrical connection 32 may be solid or rolled. In some embodiments, for reusable applications, solid pins can be used because they may be easier to clean and reprocess. In one example embodiment, as shown in FIGS. 4A and 4B, the patient-end connector 14 may not include any auxiliary connections beyond a pneumatic connector for mating with a y (wye) piece or other patient interface component. In some embodiments, the electrical connection 32 may from a part of the pre-formed components discussed above.

Figure 5A:
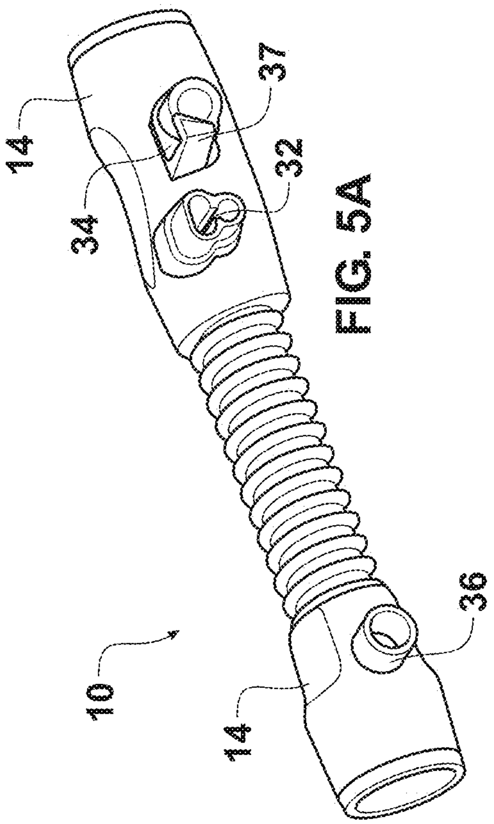
FIG. 5A is an isometric view of an embodiment of a medical tube including connectors at each end, with one of the connectors including an embodiment of a patient port and the other connector including an embodiment of a clover leaf connection and a v-notch connection.
Figure 5B:
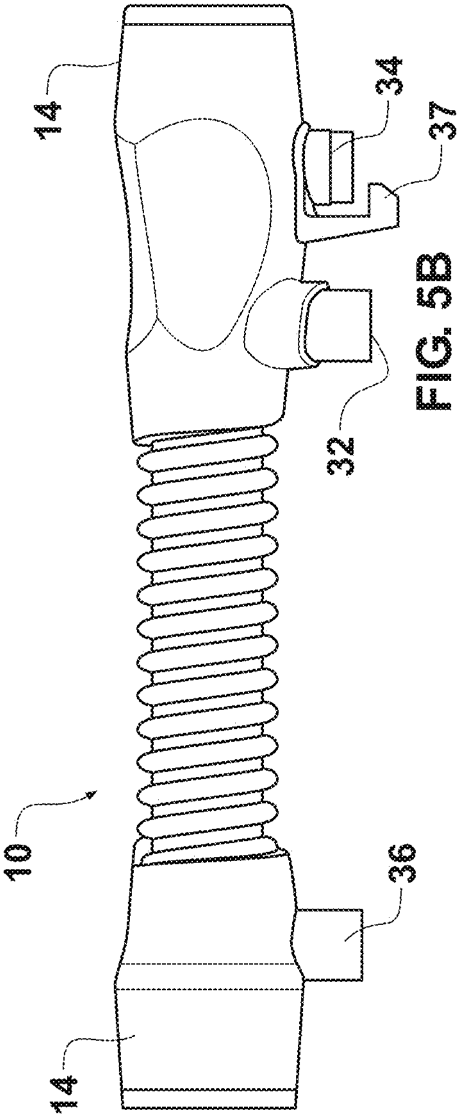
FIG. 5B is a top view of the medical tube of FIG. 5A.
Figure 5C:
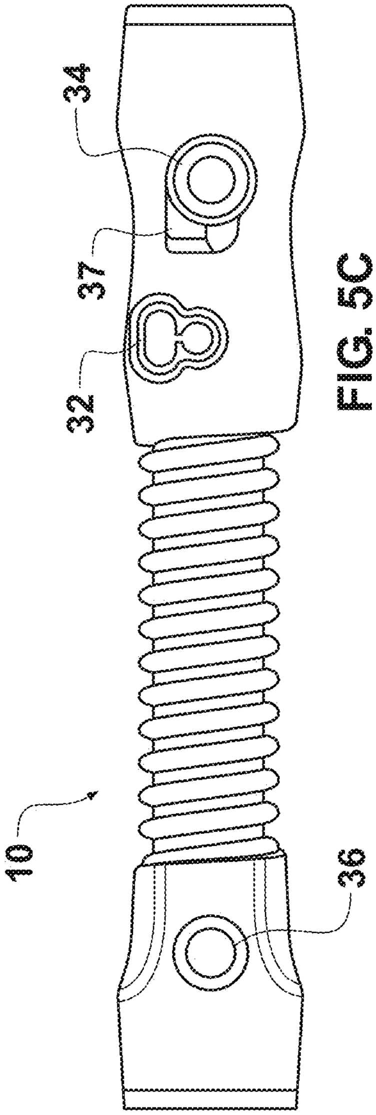
FIG. 5C is a side view of the medical tube of FIG. 5A.

FIGS. 5A, 5B, and 5C are isometric, top, and end views, respectively of an embodiment of the medical tube 10 including connectors 14 at each end. As before, the connectors 14 can be overmolded onto the tube body 16 (or attached in various other manners, as described above) and can establish pneumatic connections to the medical tube 10. In the illustrated embodiment, one of the connectors 14 includes an embodiment of a sensor probe port 36 (e.g., a patient end sensor probe port 36) and the other connector 14 includes an embodiment of the electrical connection 32 (as described above) and a sensor probe port 34. In some embodiments, the chamber end includes the electrical connection 32 and the sensor probe port 34, and the patient end is provided with the patient end sensor probe port 36. A temperature probe or sensor can be connected to or inserted into the patient end sensor probe port 36. In some embodiments, other types of sensors (e.g., humidity, flow, pressure, etc.) can be configured to attach to or be inserted into the sensor port 36. In some embodiments, the patient end sensor probe port 36 may be configured to accept more than one sensor.

The sensor probe port 34 can include a locating depression or notch that can be configured to mate with a locating tooth on a sensor probe housing to provide a predetermined location and orientation of the sensor(s) of the sensor probe housing relative to the gases flow. The sensor probe housing may include one or more sensors, such as temperature, pressure, humidity, and/or flow sensors. In some embodiments, a retention member can be provided to hold the sensor housing in place in the port 34. In some embodiments, the retention member can comprise a clip 37 (as shown). The clip 37 can comprise a flange that extends radially outward from the connector 14 adjacent the port 34, with a longitudinally extending tab that extends toward or over the port 34. The clip 37 can engage the sensor housing to secure the sensor housing to the port 34. In some embodiments, the retention member may comprise the clip 37 (as shown), a tethered cap, or a lid with integral hinging portion, etc. The retention member can be configured to prevent the sensor housing from becoming inadvertently dislodged from the port 34. Port 36 may optionally include a similar locating depression and/or retention member as described with reference to port 34. In some embodiments, the ports 34, 36 may from a part of the pre-formed components discussed above.

The sensor probe port 34 may similarly allow for one or more sensors, such as temperature, pressure, humidity, and/or flow sensors to be located in the port 34.

Respiratory Systems, Breathing Circuits, and Kits Including Medical Tubes

The medical tubes described herein (e.g., the medical tube 10 described above) can be provided in one or more respiratory systems, breathing circuits, or kits. The medical tubes may be used for delivering and/or removing humidified gases from a patient, such as in obstructive sleep apnea, neonatal, respiratory humidification, and surgical humidification systems including insufflation systems and systems for patients undergoing procedures under general anesthetic. The medical tubes can be used to deliver respiratory gases to and/or from a patient as part of a respiratory therapy or treatment. The respiratory gases may be heated and/or humidified prior to delivery to the patient in order to, for example, reduce the likelihood of infection and/or tissue damage.

FIG. 6 schematically illustrates an embodiment of respiratory system (or breathing circuit) 100A that can include one or more of the medical tubes described herein. In the illustrated embodiment, the respiratory system 100A includes a gases source 110 that is either integrated with, or a separate component from, a humidification apparatus 150 (e.g., a humidifier). The gases source 110 and/or humidification apparatus 150 supply heated and humidified gases to a patient 190 via a breathing circuit that includes, for example, an inspiratory tube 170 and a patient interface 180. As used herein, patient interface has a broad meaning and is to be given its ordinary and customary meaning to one of skill in the art, and patient interface also includes, without any limitation, any one or more of a full face mask, a nasal mask, an oral mask, an oral-nasal mask, a nasal pillows mask, nasal cannulas, nasal prongs, a laryngeal mask, or any other suitable coupling between the medical circuit and the airways of the patient.

In some embodiments, the inspiratory tube 170 can be any of the medical tubes described herein (for example, the inspiratory tube 170 can be any of the medical tubes 10 shown in FIGS. 1-5C and described above).

In some embodiments, another medical tube, such as a supply tube 130, can be used to transport gases from the gases source 110 to the humidification apparatus 150. Supply tube 130 is sometimes called a “dry” line, as it is positioned in the breathing circuit prior to the “wet” humidifier. In some embodiments, the supply tube/dry line 130 can be any of the medical tubes described herein (for example, supply tube 130 can be any of the medical tubes 10 shown in FIGS. 1-5C and described above). In one example embodiment, the dry line 130 may be as pictured in FIG. 1. Although the tube of FIG. 1 may include at least one wire in bead 16, it should be appreciated that such wire(s) may not be provided with connectors for a power supply, and in this way, may be present but not used for heating and/or sensing functions. Alternatively, the dry line 130 may be as pictured in FIGS. 4*a*-5*c*, where the wire(s) may be enabled to be used if the appropriate connections are made at the relevant ports 34, 36 on the connectors 14. In some embodiments, an additional tube, such as an interface tube 185, can connect between the inspiratory tube 170 and the patient interface 180. In some embodiments, the interface tube 185 can be any of the medical tubes described herein (for example, interface tube 185 can be any of the medical tubes 10 shown in FIGS. 1-5C and described above). It is to be understood that other variations from the system 100A shown may exist. For example, the inspiratory tube 170 may comprise multiple sections to accommodate other equipment such as a water trap, an intermediate connector with one or more sensors, a PCB, and/or a controller.

FIG. 7 schematically illustrates another embodiment of respiratory system (or breathing circuit) 100B that can include one or more of the medical tubes described herein. In many respects, the respiratory system 100B can be similar to the respiratory system 100A of FIG. 6. For example, as illustrated, the respiratory system 100B includes a gases source 110 and a humidification apparatus 150 (e.g., a humidifier). The gases source 110 and/or humidification apparatus 150 supplies heated and humidified gases to a patient 190 via a breathing circuit that includes, for example, an inspiratory tube 170 and a patient interface 180. In FIG. 7, however, the breathing circuit further includes an expiratory tube 172, by which exhaled gases can be transported. In some embodiments, the expiratory tube 172 transports exhaled gases back to the gases source 110 and/or humidification apparatus 150. In some embodiments, the expiratory tube 172 can be any of the medical tubes described herein (for example, the expiratory tube 172 can be any of the medical tubes 10 shown in FIGS. 1-5C and described above). In one further example embodiment, the expiratory tube 172 is the heated medical tube shown in FIGS. 4A-B.

In the illustrated embodiment of FIG. 7, the connector 175 can comprise a y (wye) piece that connects both the inspiratory tube 170 and the expiratory tube 172 to a patient interface component, such as the interface tube 185 (as shown in FIG. 6), or directly to the patient interface 180 itself. Further, the respiratory system 100B can include one or more sensors 135. For example, a sensor 135 can connect to the inspiratory tube 170 near the patient interface 180 or a sensor 135 can connect to the patient interface 180, among other possible sensor locations. The sensor 135 can be integrated into or connectable to the inspiratory tube 170. In the illustrated embodiment, the system 100B includes two sensors 135, with a first sensor 135 positioned at or nearby to the humidifier chamber outlet end of the inspiratory tube 170, and a second sensor 135 positioned at the patient end of the inspiratory tube 170. In some embodiments, the inspiratory tube 170 can comprise the medical tube 10 shown in FIGS. 5A-5C and the sensors 135 can be connected to the sensor ports 34, 36. Alternatively or in addition, sensor(s) 135 may be provided at or nearby to the humidifier chamber inlet. A signal provided by the sensor(s) 135 can be provided, for example, to a control system. In some embodiments, the sensor(s) 135 comprises one or more of a temperature sensor, a humidity sensor, a flow sensor, and a pressure sensor. Although the sensors 135 are illustrated connected to the patient end and chamber outlet of the inspiratory tube 170, one or more sensors can be included, alternatively or additionally, in other locations on the inspiratory tube 170 and/or on other medical tubes or components in the respiratory system.

It is to be understood that other variations from the system shown may exist. For example, the inspiratory 170 and/or expiratory tube 172 may comprise multiple sections to accommodate other equipment such as a water trap, an intermediate connector with one or more sensors, a PCB, and/or a controller. In another example embodiment, the system may include a nebulizer or a port therefore. In another example embodiment, the system may include a catheter mount or an exhalation valve.

In some embodiments, the medical tubes described herein can be provided in a kit, such as a circuit kit. A kit may include, for example, one or more medical tubes as described herein as well as one or more of the following: a dry line, a chamber, a water trap, a y (wye) piece, various adapters, wires, and sensors. In certain kits, the medical tubes may be provided as inspiratory tubes and/or expiratory tubes and/or dry lines and/or tube extensions or segments for use in systems with water traps.

In some embodiments, the kits or systems can include an expiratory tube that is breathable. For example, an expiratory tube can be made from a breathable material. As used herein, a "breathable material" generally refers to a material that is permeable to moisture vapor and substantially impermeable to liquid moisture and the bulk flow of gases. In certain embodiments, a breathable material has a moisture (water) vapor transmission rate greater than or equal to 650 $g/m^2/day$ (or thereabout) when measured according to Procedure B of ASTM E96 (using the upright cup method at a temperature of 23° C. and a relative humidity of 50%). However, in some embodiments, other materials that do not meet this definition may also be considered to be breathable.

Although this disclosure has been described in the context of certain embodiments and examples, it will be understood by those skilled in the art that the disclosure extends beyond the specifically disclosed examples to other alternative examples and/or uses and obvious modifications and equivalents thereof. In addition, while several variations have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one example can be used with a different example described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Unless the context clearly requires otherwise, throughout the description and the claims, the words "comprise," "comprising," and the like, are to be construed in an inclusive sense as opposed to an exclusive or exhaustive sense, that is to say, in the sense of "including, but not limited to." Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Recitations of quantities, dimensions, sizes, formulations, parameters, shapes and other characteristics should be construed as if the term "about" or "approximately" precedes the quantity, dimension, size, formulation, parameter, shape or other characteristic. The terms "about" or "approximately" mean that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. Recitations of quantities, dimensions, sizes, formulations, parameters, shapes and other characteristics should also be construed as if the term "substantially" precedes the quantity, dimension, size, formulation, parameter, shape or other characteristic.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4," and "3 to 5," etc.

The invention may also be said broadly to consist in the parts, elements and features referred to or indicated in the specification of the application, individually or collectively, in any or all combinations of two or more of said parts, elements or features.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined by the claims that follow.

What is claimed is:

1. A medical tube for transporting gases, the medical tube comprising:

a tube body comprising:

a bead comprising a substantially flat surface, the bead further comprising two heating wires disposed within the bead, the bead positioned such that the substantially flat surface forms a first portion of a lumen wall of the medical tube with the bead disposed along a helical path wherein successive revolutions of the helical path are spaced apart by a bead pitch distance with respect to a longitudinal axis of the tube body; and a film, a first portion of the film laid over the bead and a second portion of the film forming a second portion of the lumen wall; and a connector overmolded onto a first end of the tube body, a first end of the connector overlapping the tube body and directly contacting the film, a portion of the first end of the connector being aligned with the bead along a helical portion of the tube body and comprising an edge offset by the bead pitch distance, wherein the lumen wall, formed by the substantially flat surface of the bead and the second portion of the film, comprises a substantially smooth bore such that the substantially flat surface of the bead and the second portion of the film are aligned when the medical tube is straight along a longitudinal axis of the medical tube.

2. The medical tube of claim 1, wherein the second portion of the film comprises a substantially flat surface forming the second portion of the lumen wall.

3. The medical tube of claim 2, wherein the substantially flat surface of the bead and the substantially flat surface of the second portion of the film are substantially aligned.

4. The medical tube of claim 1, wherein a cross-section of the bead is substantially D-shaped, triangular, square, trapezoidal, equilateral, or polygonal.

5. The medical tube of claim 1, wherein the bead comprises at least one sensor wire for conveying power and/or data between at least one sensor and a controller.

6. The medical tube of claim 1, wherein at least one of: the bead comprises a thermoplastic elastomer (TPE); or the film comprises a thermoplastic elastomer (TPE).

7. The medical tube of claim 1, wherein the film comprises a plurality of layers.

8. The medical tube of claim 7, wherein each of the plurality of layers comprises a winding of the film.

9. The medical tube of any of claim 7, wherein a first layer of the plurality of layers overlaps a second layer of the plurality of layers over an outer surface of the bead to form an overlapping portion.

10. The medical tube of claim 9, wherein the overlapping portion overlays between 55% and 95% of the outer surface of the bead.

11. The medical tube of claim 7, wherein a first layer of the plurality of layers and a second layer of the plurality of layers overlap over an outer surface of a first winding of the bead, and the first layer and a third layer of the plurality of layers overlap over an outer surface of a second winding of the bead, the second winding adjacent to the first winding to form an overlapping portion.

12. The medical tube of claim 11, wherein the overlapping portion overlays at least half of the outer surface of each of the first winding of the bead and the second winding of the bead.

13. The medical tube of claim 11, wherein the overlapping portion overlays between 55% and 95% of each of the first winding of the bead and the second winding of the bead.

* * * * *